(12) United States Patent
McCarthy et al.

(10) Patent No.: US 8,394,766 B2
(45) Date of Patent: Mar. 12, 2013

(54) CELLULAR ACTIVATION INSULIN THERAPY

(76) Inventors: Michael McCarthy, Ontario (CA); Marc Rose, Costa Mesa, CA (US)

( * ) Notice: Subject to any disclaimer, the term of this patent is extended or adjusted under 35 U.S.C. 154(b) by 0 days.

(21) Appl. No.: 12/968,120

(22) Filed: Dec. 14, 2010

(65) Prior Publication Data

US 2011/0144011 A1   Jun. 16, 2011

Related U.S. Application Data

(60) Provisional application No. 61/286,313, filed on Dec. 14, 2009.

(51) Int. Cl.
*A61K 38/28* (2006.01)
*A61P 3/10* (2006.01)

(52) U.S. Cl. .............................. 514/5.9; 514/6.8; 514/6.9

(58) Field of Classification Search .................. None
See application file for complete search history.

(56) References Cited

U.S. PATENT DOCUMENTS

| | | | | |
|---|---|---|---|---|
| 4,137,320 | A * | 1/1979 | Tedeschi | 514/368 |
| 6,579,531 | B2 | 6/2003 | Aoki | |
| 6,582,716 | B2 | 6/2003 | Aoki | |
| 6,613,342 | B2 | 9/2003 | Aoki | |
| 6,613,736 | B2 | 9/2003 | Aoki | |
| 6,821,527 | B2 | 11/2004 | Aoki | |
| 6,967,191 | B2 | 11/2005 | Aoki | |
| 7,682,351 | B2 | 3/2010 | Aoki | |
| 2003/0232748 | A1 * | 12/2003 | Langkjaer | 514/3 |
| 2006/0122099 | A1 * | 6/2006 | Aoki | 514/3 |

OTHER PUBLICATIONS

Normedex, "We will Stop Diabetes Complications", Brochure for Pulsatile Intravenous Therapy, NorMedex, Enhancing the quality of life, Irvine, CA, (c) NorMedex Centers, LLC, 2006.
Smith, S.J., "In the Matter of the Consolidated Appeals of Denial of Coverage for Hepatic Activation Treatment, CA Public Employees' Retirement System (CalPERS)", Board of Administration, Case No. 3490-5, 3490-3, 3490-2, 3490-1, 3490-4, and 3490-6, Jan. 2002.
Normedex, "Pulsatile Intravenous Insulin Therapy (PIVIT)—Rescue Treatment for Serious Complications of Diabetes", (c) NorMedex Centers, LLC, 2007.
Patent Cooperation Treaty, "Notification of Transmittal of the International Search Report and the Written Opinion of the International Searching Authority, or the Declaration", Jan. 20, 2012.

* cited by examiner

*Primary Examiner* — Gyan Chandra
(74) *Attorney, Agent, or Firm* — Fish & Associates, PC

(57) ABSTRACT

Diabetic and other patients are treated using an aggressive form of Pulsed Insulin Therapy in which a pre-treatment blood sugar level in the patient of at least 250-300 mg/dL, and the patient is treated with at least first and second cycles, each cycle comprising (1) pulsing a recombinant human insulin to the patient in concentrations of more than 10% to achieve a target intra-treatment blood sugar level (BSL) swing of more than 100 mg/dL, and (2) raising the blood sugar level to at least 250-300 mg/dL.

10 Claims, 1 Drawing Sheet

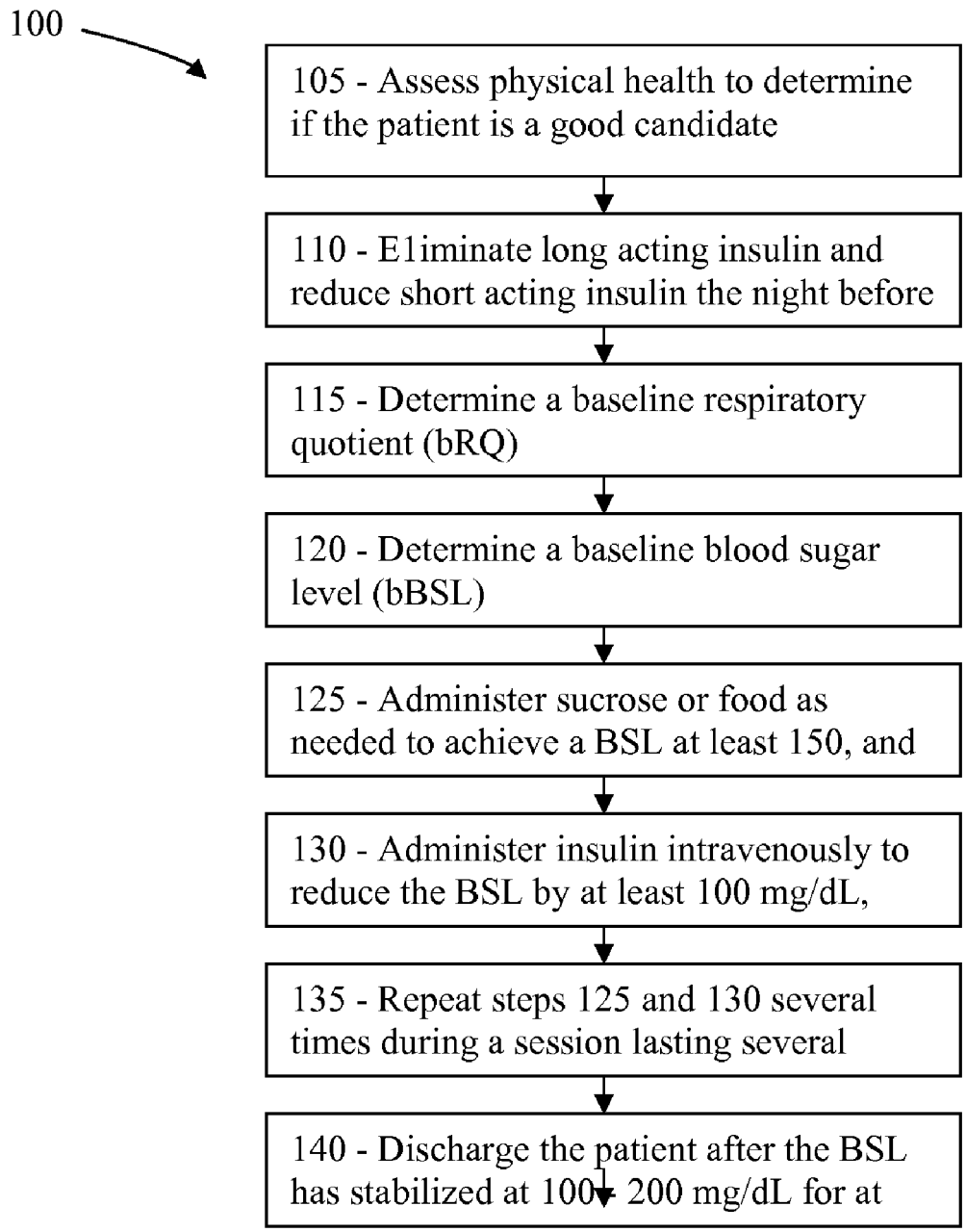

CELLULAR ACTIVATION INSULIN THERAPY

This application claims priority to U.S. Provisional Application No. 61/286,313 filed Dec. 14, 2009, which is incorporated herein in its entirety.

FIELD OF INVENTION

The field of the invention is Pulsed Insulin Therapy.

BACKGROUND OF THE INVENTION

The core concept of Pulsed Insulin Therapy has been known for at least 20 years, by various names including Pulsatile Intravenous Insulin Therapy (PIVIT), Chronic Intermittent Intravenous Insulin Therapy (CIIIT), Metabolic Activation Therapy (MAT), and Hepatic Activation. In such therapies a patient's blood sugar is raised and lowered by about 50 to 75 mg/dL over a period of several hours by alternating between doses of insulin and sugars or high carbohydrates foods. Although the mechanisms of action have not been clearly elucidated, it is apparent from the clinical results that the technique has usefulness in treating diabetic implications, including blindness and other ocular manifestations, nerve disease, cardiovascular disease, diabetic nephropathy, and poor wound healing.

There are several patents and patent applications of relevance, particularly those to Thomas T. Aoki, including for example U.S. Pat. Nos. 6,579,531, 6,582,716, 6,613,342, 6,613,736, 6,821,527, 6,967,191, and 7,682,351. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Given the long history of these procedures, one would have expected that the treatment parameters would have been optimized long ago to produce the most favorable results. It turns out, however, that the known treatment parameters are insufficient in that regard. What is needed are systems and methods that produce superior results to those previously obtainable.

SUMMARY OF THE INVENTION

The inventive subject matter provides apparatus, systems and methods in which Pulsed Insulin Therapy is administered aggressively, implementing a protocol that includes one or more of the following features: (1) pulsing insulin to the patient in concentrations of more than 10%; (2) utilizing fast acting human insulin as opposed to porcine or other insulin; and (3) targeting intra-treatment blood sugar level (BSL) swings of at least 100 mg/dL and preferably at least 125 mg/dL or at least 150 mg/dL.

In view of the considerable strain that Pulsed Insulin Therapy puts on liver and other tissues, the results of aggressive PIT, which we call Cellular Activation Insulin Therapy (CAIT), are surprising good. Among other things, treatment objectives can be achieved in weeks instead years of treatment.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 1 is a schematic of steps in a preferred protocol.

DETAILED DESCRIPTION

In FIG. 1, a preferred protocol 100 generally includes the following steps:
- 105—Assess physical health to determine if the patient is a good candidate;
- 110—Eliminate long acting insulin and reduce short acting insulin the night before;
- 115—Determine a baseline respiratory quotient (bRQ);
- 120—Determine a baseline blood sugar level (bBSL);
- 125—Administer sucrose or food as needed to achieve a BSL at least 150, and more preferably at least 300 mg/dL;
- 130—Administer insulin intravenously to reduce the BSL by at least 100 mg/dL, using clinical observation, BSL and RQ as guides;
- 135—Repeat steps 125 and 130 several times during a session lasting several hours; and
- 140—Discharge the patient after the BSL has stabilized at 100-200 mg/dL for at least 30 minutes.

In Step 105, patients are evaluated for whatever factors appear to be appropriate, which include assessments of overall health, history of diabetes, and signs and symptoms of diabetic complications. So far there are no rigorous guidelines other than those discussed herein, in conjunction with safety concerns, and the practical experience and common sense of the treating physician. In general, individuals having a longer history of diabetes, those having a larger body mass index (BMI), older individuals, and those having greater incidence of diabetic complications will need to be given higher doses of insulin to achieve the desired swings in blood sugar contemplated by Cellular Activation Insulin Therapy.

When beginning Cellular Activation Insulin Therapy, one should inquire and record prior incidences of hypoglycemia. If patient is under recent, prior Cellular Activation Insulin Therapy treatment care, then incidences since the last treatment should also be recorded. One should also note possible precipitating factors: e.g. lack of total intake calories (not eating in timely manner), pronounced increased physical activity and/or change in insulin dose (specific to insulin users) however pertinent to all glucose lowering medications (e.g. glucophages). If small incremental increases of insulin are suspected to cause the reaction of a greater than 20% difference, this denotes hypoglycemic episode risk, and would tend to lead the treating physician to be somewhat less aggressive in treatment than he/she would otherwise tend to be. It would also be advisable to check BSL and possibly RQ somewhat more often that otherwise.

In Step 110 the patient is instructed to eliminate long acting insulin and reduce short acting insulin by at least 50% the night before the treatment begins. That allows the blood sugar level to rise, which on the day of treatment is preferably between 200 mg/dL and 300 mg/dL, but can rise to rise 500 mg/dL or even higher at the start of treatment. Given the wide range of conditions encountered in different patients, and even in a given patient at different times, the extent to which short acting insulin is reduced should be guided by the knowledge and experience of the treating physician.

In Step 115 a baseline respiratory quotient (bRQ) is determined. RQ is the ratio of the volume of carbon dioxide released, to the volume of oxygen consumed, by a body tissue or an organism at a given point in time, (RQ=VCO2/VO2). In general, the oxidation of carbohydrate results in an RQ of 1.0;

of fat, 0.7; and of protein, 0.8. An RQ greater than 1.0 indicates anaerobic metabolism. bRQ can be measured in any suitable manner, including use of a respirometer. Some of the prior art specifies specific strategies for determining bRQ, such as testing RQ every five minutes until a stable baseline reading is obtained. Rigorous utilization of any specific strategy is, however, deemed unnecessary for Cellular Activation Insulin Therapy, and baselines can, for example, be established by making multiple RQ determinations at intervals other than five minutes. In particular, if first and second RQ determinations vary considerably, it is desirable to wait more than five minutes before making a third RQ determination. Nor is a particularly stable bRQ necessary to begin the pulsed administration of insulin.

In Step 120 a baseline blood sugar level (bBSL) is determined. Blood sugar level is a measurement of sugar (mostly glucose) in the circulating blood of a patient. All suitable devices are contemplated for this purpose, including a typical finger stick monitor, and a continuous blood glucose monitor.

In general, the intra-session treatment goal is to keep BSL between 150-300 mg/dL throughout treatment hours. If the initial pre-treatment BSL is under 100 mg/dL, no treatment should be commenced until such time as the BSL safely is above 150 mg/dL BSL, and more preferably above 300 mg/dL. In some cases, the patient may need to be rescheduled (this point is for diabetics only). In best cases, diabetics should review their diet and insulin dosage adjustments should be made to ensure fasting BSL's present as equal to or greater than 150 mg/dL. Treatment should never commence when a patient's BSL is less than 100 mg/dL.

In Step 125 sucrose or food is administered as needed to achieve a BSL at least 150, and more preferably at least 300 mg/dL. At the start of Cellular Activation Insulin Therapy it may not be necessary to artificially raise the blood sugar level at all, because many patients will already have high BSLs from having eliminated long acting insulin and/or reduced short acting insulin the night before. In other cases, such as where the patient has fasted since the previous dinner, the bBSL may be only about a 60-100 mg/dL. Usually, however, the patient is directed not to fast, but instead to have a large high carbohydrate breakfast, such a pancakes with syrup before coming to the clinic. If the bBSL is below about 200 mg/dL, Cellular Activation Insulin Therapy contemplates the patient ingesting additional sugars or foods to raise the bBGL.

One aspect that is different from the prior art is that the preferred substances for raising blood sugar levels in Cellular Activation Insulin Therapy are high carbohydrate foods, then sucrose, or possibly mannose or fructose, rather than glucose. For unknown reasons use of carbohydrates other than glucose seems to have a greater effect in stimulating liver carbohydrate metabolism than pure glucose, and while not wishing to be limited to any particular theory or mechanism of action, it is contemplated that the need for the liver to convert the fructose component of sucrose into glucose is a contributing factor to the surprisingly strong results achieved with Cellular Activation Insulin Therapy. Regardless of what combination of sugar(s) and/or food is given during Step 125, a patient typically receives about 101 to 180 gm of carbohydrate during each cycle, and as with other treatment parameters discussed herein, the amounts given are at the discretion of the treating physician in accordance with a desire to pursue aggressive treatment relative to the particular condition of the patient.

In Step 130, insulin is administered intravenously to reduce the BSL by at least 100 mg/dL, using clinical observation, BSL and RQ as guides. Physically, this is accomplished as follows. An IV line is established, then a pump is connected, with its attached pre-filled syringe, loaded with the appropriate dilution of insulin (2 ml. short acting insulin: to 8 ml. of normal saline). Contemplated dilutions include 1:9, 0.5:9.5, 0.25:9.75, 0.125:9.875, 0. and 0625:9.9375 depending on severity of disease condition or pancreatic dysfunction suspected liver malfunction) Note: If a patients BSL continues to drop even at lowest dose setting, the concentration must be lowered from 2:8 to 1:9 and so on. When starting the treatment, all patients with a BSL below 300 mg/dL are given an appropriate sugar loading dose. Treatment should be safely started with caution when a patients BSL<150 mg/dL. Blood sugar level is generally tested at greater than 30 minute intervals throughout treatment hours.

Where sucrose is used to increase BSL, the following dosing schedule is suggested, which as mentioned elsewhere herein may be adjusted in accordance with individual patient responses.

TABLE 1

| BSL | gm sucrose |
| --- | --- |
| 150-199 mg/dL | 40 grams of sucrose |
| 200-249 mg/dL | 30 grams of glucose |
| 250-299 mg/dL | 20 grams of glucose |
| 300-550 mg/dL | 10 grams of glucose |
| >550 mg/dL | contact patient's primary care physician |

Where carbohydrate is administered other than as pure sucrose, then approximately equivalent amounts of carbohydrate are to be used. Treatment goals are to maintain BSL in the 150 mg/dL to 300 mg/dL therapeutic range AND sucrose ingested for each treatment hour between 60-100 grams. When this is achieved, maintain the current pulsed dose quantity for the remaining pulses for that treatment hour. If BSL rises over 300 mg/dL at anytime during the treatment hour: stop the pump, reprogram dosage higher by 2 mu/kg and immediately resume pump treatment. If the BSL drops by greater than 75 mg/dL during a treatment hour, give sucrose per dosing schedule and repeat BSL's every 15 minutes. If not returned to the treatment range, give further sucrose, per dosing schedule, and continue to evaluate BSL every 15 minutes until patient reaches the optimum treatment range, 150 mg/dL-300 mg/dL.

Once a patient's body responses become apparent, the regimen should be adjusted accordingly as follows:
Type 1 Diabetic Patients (or Type II being Treated as a Type I, e.g. Insulin Injecting).

Using BMI measurements as a guideline, compare the patient's actual BMI with BMIs below 18.5, 18.5 to 25, 25 to 30, and over 30. BMI below 18.5. These patients typically take up to a total of 40 units of insulin daily and are of ectomorphic habitus description. They readily respond to small doses of insulin and prone to hypoglycemia. They are often termed "brittle" diabetics. Subgroups of ectomorphic patients are petite or tall and lanky (low body fat). They are extremely sensitive to advancing insulin dosages (prone to hypoglycemia) until they begin to gain weight over the weekly continuing treatments or until their 02 consumption vs. C02 production symmetrically raises. Treatment: After receiving sucrose based on the previous chart, begin pulse dosages at 10 mU/kg. Record BSL every 30 minutes, keeping the patient "in BSL range." Administer sucrose according to schedule during the treatment range (45-90 minutes). After completion of the first hour perform resting RQ to obtain V02/VC02 and record. The patient completes 3 treatment hours with one hour "rest" periods between treatment hours.

The pulse doses increase by 2 mU/kg each treatment session, as long as, the BSL remains in the ideal range with sucrose administration. These patient's rarely exceed 26 mU/kg treatment dosing. It may take up to 6 months to reach optimal doses for treatment sessions. The third treatment hour session is conducted similarly. IT IS IMPORTANT TO NOTE THAT THESE PATIENTS MUST REMAIN FOR ONE HOUR AFTER THE LAST TREATMENT PERIOD. This is so BSL is done every 15-30 minutes and sucrose is given to keep BSL appropriate to treatment level. The patient may not be discharged until there are two consecutive (stable)
BSL's above 150 mg/dL with the Second Level Higher than the Last. BMI Between 18.5-25

These patients are of average body habitus and typically use between 40-80 units of insulin per day. Their starting dose is 12 mU/kg. Follow the above schedule. These patients tolerate 2 mU/kg increases in pulse doses and normally do not exceed 26 mU/kg. It may take up to 4 months to achieve their optimum dosage levels. BMI between 25-30: These patients are "chubby" to obese and include endomorphic body types who often use between 40-120 units of insulin total daily dosage. Morbid obesity is not typical of Type 1 diabetics and often need higher pulsed doses than other Type 1 patients.
Type II & III Diabetics and all Extremely Low V02/VC02 Patients These patients have variable body habitus, ranging from thin to morbidly obese. Typically, their insulin requirements are higher than type 1 diabetics (50-over 200 \units daily). Their starting and eventual CAIT dosing is often higher 26 mU/kg to 34 mU/kg. They are less prone to hypoglycemia as dose rate increases. Be aware that as these patients now can lose weight, the doses of insulin needed early in treatment may need to be lowered. Note: patients on antihypertensives usually need less medication after a few weeks of treatment. Their physicians need to be alerted to this in order to avoid hypotensive episodes. Insulin doses and oral agents will almost always need to be reduced as the patient continues on regular CAIT treatments BMI (Body Mass Index) is calculated using weight and height and can be done in English or Metric units. English: BMI=(weight in pounds/height in inches squared)×703 Metric: BMI=(weight in kg! height in centimeters squared)×10.000 An online calculator for BMI is available at; http://www.cdc.gov/nccdphpidnpalbmi/calcbmi.htm In some prior art references the RQ is measured at 30 minute time intervals, but such slavish routine is neither necessary nor appropriate. An experienced physician can judge for himself/herself from clinical signs and symptoms when RQ should best be determined.

Prior art references also insist that BSL be determined at time intervals of 30 minutes or less, (i.e, at least every 30 minutes), but here again the present inventors have appreciated that such slavish routine is neither necessary nor appropriate. Indeed, their experience is that BSL need only be determined at time intervals greater than 30 minutes, as for example at intervals of 35 or 45 minutes.

Prior art references are still further insistent that insulin be administered at regular intervals, and at 6 minute intervals in particular. That is unnecessary, and possibly undesirable. First, while certain pumps preferred in the prior art are designed to administer drugs at regular intervals (e.g., the Bionica™ MD-110 pump), there is no need for such regularity. Instead of administering insulin at regular intervals of 6 min during an hour or so of treatment, it is contemplated that for Cellular Activation Insulin Therapy, insulin can be administered at irregular intervals, for example at 5 min, 6 min, 7 min, 4 min, etc, with an average time interval that may or may not equate to about 6 minutes.

One issue of significance is that many current pumps can only administer fluids at a minimum dosage of 10 units per pulse, and perhaps a maximum dosage of 56 units per pulse. That lower limit would be too much insulin for a typical patient, so that the insulin being pulsed needs to be diluted. In general, for use with pumps having minimum pulses of 10 units, it has been found that individuals who have been diagnosed with diabetes up to five years should receive a relatively low insulin concentration (10% insulin±3%), those having been diagnosed with diabetes more than 5 years should receive a significantly higher insulin concentration (20% insulin±3%). Patients having recalcitrant diabetes should be given an even higher insulin concentration (30% insulin±3%). Patients who have never been diagnosed with diabetes should receive a concentration of insulin according to the experience of the physician, and may well range from a concentration of 0.5% insulin to a concentration of 40% insulin±3%.

Yet another improvement in Cellular Activation Insulin Therapy is the use of recombinant human insulin, such as Humulin®. Humulin reaches peak activity rapidly dependent on dose, site, temperature and a short duration of activity. Other suitable insulins are contemplated to include Novolin N®, Insulatard®, Protaphane®, Insuman Basal®, and ReliOn/Novolin NPH®. The prior art uses Humalog® or Novolog®) or even Regular insulin. Humalog peaks at about 75 minutes, Novolog reaches peak activity at 52 minutes, and Regular insulin peaks at about 145 minutes (2 hours and 25 minutes) for regular insulin. (Eur J Clin Pharmacol 1999 May; 55(3):199-203). These differences are significant because, among other things, the current inventors have discovered that the slope of the BSL curve, and not just extent of the BSL drop, is extremely significant in achieving the results seen with the superior results seen with Cellular Activation Insulin Therapy.

As discussed above, the amount of insulin is administered to reduce the BSL by at least 100 mg/dL, using clinical observation, BSL and RQ as guides. In general, inferior reduction (<50 mg/dL) of BSL after one hour administration of pulsed insulin or subsequent ½ hour (resting) time off active pulsation of insulin would lead the attending physician to administer a higher concentration of insulin, a greater total amount of insulin, and/or a faster administration of insulin during the next cycle. The reverse is also true. An especially high reduction (<200 mg/dL) of BSL after one hour administration of pulsed insulin or subsequent ½ hour (resting) time off active pulsation of insulin would lead the attending physician to administer a lower concentration of insulin, a lower total amount of insulin, and/or a slower administration of insulin during the next cycle.

In Step 135 the steps 125 and 130 are repeated several times during a treatment session lasting several hours. In general, an approximately 5 hour session involves 3 or 4 periods of hours of IV insulin administration spaced by a total of up to 2 hours of rest. For example, a patient might receive four cycles of IV insulin administration for 45 minutes and a half hour rest, for a total of 5 hours. Another patient might receive three cycles of IV insulin administration for 1 hour and 45 minutes rest for a total of 5.25 hours. In general, the maximum BSL drop during the insulin administration phase of any given cycle should be approximately 200 mg/dL, with the recognition that in early treatment cycles the BSL drop of particularly recalcitrant cases may be as low as zero.

The current inventors recommend against a rigorous, preset schedule, in favor of schedules tailored to particular situations, with the attending physician initiating and modifying protocols based on patient history, current patient health status, and signs and symptoms during treatment. Following are several specific examples, outlining the course of treatment, and the most salient reasons for following specific schedules.

Example 1—a 63 year old female patient presented with numerous diabetic complications, including peripheral neuropathy and various diabetic wounds (that have not healed over 3 years of conventional medical treatment). She had been diagnosed as a diabetic for 23 years, and was taking metformin 500 mg BID. On the first day of treatment her weight 71 kg., blood pressure 110/68, and pulse 78. In her first cycle she was given 32 mUnits of rDNA Insulin every 4-7 minutes for a total of 274 mUnits over 45-90 minutes. During that first cycle her BSL went from 251 to 86, 60 gms sucrose given and her RQ went from 0.67 to 0.69. She was then given 30-40 minutes of rest. During the second cycle the patient was given 32 mUnits of rDNA Insulin every 4-7 minutes for a total of 274 mUnits over 45-90 minutes. During that second cycle her BSL went from 207 to 140, and her RQ went from 0.69 to 0.72. She was then given 30-45 minutes of rest. During the third cycle the patient was given 28 mUnits of rDNA Insulin every 4-7 minutes for a total of 239 mUnits over 45-90 minutes. During that third cycle her BSL went from 262 to 139, and her RQ went from 0.72 to 0.91. Those particular treatment parameters were chosen because her long history of severe diabetic complications, including hypostatic hypertension.

Example 2—a 73 year old male patient presented with numerous diabetic complications, including cardiomyopathy. He had been diagnosed as a diabetic for 33 years, and was taking a multiplicity of diabetic and cardiac medications. On the first day of treatment his weight 87 kg, blood pressure 142/50, and pulse 67. In his first cycle he was given 36 mUnits/kg of rDNA Insulin every 4-7 minutes for a total of 308 mUnits over 45-90 minutes. During that first cycle his BSL went from 334 to 177, and his RQ went from 0.75 to 0.78. He was then given 30-45 minutes of rest. During the second cycle the patient was given 36 mUnits of rDNA Insulin every 4-7 minutes for a total of 86 mUnits over 45-90 minutes. During that second cycle his BSL went from 210 to 157, and his RQ went from 0.78 to 0.82. He was then given 30-45 minutes of rest. During the third cycle the patient was given 34 mUnits of rDNA Insulin every 4-7 minutes for a total of 291 mUnits over 45-90 minutes. During that third cycle his BSL went from 257 to 181 and his RQ went from 0.78 to 0.95. Those particular treatment parameters were chosen because of the patient's history of disease, cardiomyopathy, nephropathy and peripheral neuropathy.

Example 3—a 61 year old male patient presented with numerous diabetic complications, including extreme fatigue. He had been diagnosed as a diabetic for 18 years, and was taking nothing other than bland diet. On the first day of treatment his weight 78 kg, blood pressure 135/92, and pulse 86. In his first cycle he was given 18 mUnits of rDNA insulin every 4-7 minutes for a total of 154 units over 45-90 minutes. During that first cycle his BSL went from 339 to 244 and his RQ went from 0.82 to 0.90 He was then given 30-45 minutes of rest. During the second cycle the patient was given 28 mUnits of rDNA insulin every 4-7 minutes for a total of 239 mUnits over 45-90 minutes. During that second cycle his BSL went from 239 to 181 and his RQ went from 0.90 to 1.02 He was then given 30-45 minutes of rest. During the third cycle the patient was given 24 mUnits of rDNA insulin every 4-7 minutes for a total of 205 mUnits over 45-90 minutes. During that third cycle his BSL went from 176 to 138 and his RQ went from 1.02 to 1.06. Those particular cycle times and insulin injection amounts were also chosen because of the patient's long history of disease and numerous diabetic complications.

In Step 140 the patient is discharged after the BSL has stabilized at 150-200 mg/dL for at least 30 minutes. The reason for delay in discharge is that the aggressive treatment of Cellular Activation Insulin Therapy may well lead to a "hot liver", one that has been "kick started" to metabolize carbohydrate at a very rapid rate. Failure to ensure that the patient is sufficiently stabilized, for example, might lead to a patient leaving the office with a BSL of 125 mg/dL, only to have that level fall to 75 mg/dL by the time the patient gets into his/her car to drive home.

As noted above, it is known in the prior art to treat diabetic complication using the various forms of Pulsed Insulin Therapy. Such treatments typically continue weekly or monthly for many years. Surprisingly, the current inventors have discovered that the more aggressive Cellular Activation Insulin Therapy can treat many other conditions that have not previously been associated with Pulsed Insulin Therapy, as for example, ankylosing spondylitis, rheumatoid arthritis, lupus and other autoimmune diseases, and possibly many of the etiology unknown pain conditions, as well as neuro-affected diseases. It is contemplated that a common denominator among all these conditions is increased systematically diffuse inflammation is one consequence commonly seen as inflammatory markers, e.g., hemoglobin A1c and C-reactive protein.

For example, in the experimentation leading to this application, the current inventors have achieved, among many other things, the following unexpected results: complete remission of pain and movement restriction in an ankylosing spondylitis patient; significant reduction of blood cancer markers in two cancer patients; and significant restoration of energy and vitality restored to substantially all of the aged patients. In one particular case there was a significant reversal of all dystonia in a Parkinson's patient, but only while the patient was being treated. Symptoms returned within 30 minutes post treatment.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:
1. A method of treating a patient in need thereof, comprising:
    establishing a pre-treatment blood sugar level in the patient of at least 250-300 mg/dL; and treating the patient with at least first and second cycles, each cycle comprising (1) pulsing a fast-acting insulin to the patient in a concentration of 10%+3% such that each of the first and second cycles targets to achieve a target intra-treatment blood sugar level (BSL) swing of more than 100 mg/dL, and (2) raising the blood sugar level to at least 250-300 mg/dL by administering carbohydrate.

2. The method of claim 1, wherein the fast acting insulin comprises a recombinant human insulin.

3. The method of claim 2, wherein the concentration of insulin being pulsed is 20% insulin±3%.

4. The method of claim 2, wherein the concentration of insulin being pulsed is 30% insulin±3%.

5. The method of claim 2, wherein the concentration of insulin being pulsed is 40% insulin±3%.

6. The method of claim 1, wherein the target intra-treatment blood sugar level (BSL) swing of at least 125 mg/dL.

7. The method of claim 1, wherein the target intra-treatment blood sugar level (BSL) swing of at least 150 mg/dL.

8. The method of claim 1, wherein the step of raising the blood sugar level comprises administering sucrose to the patient.

9. The method of claim 1, wherein the step of raising the blood sugar level comprises administering food to the patient.

10. The method of claim 1, further comprising pulsing the insulin to the patient at irregular intervals.

\* \* \* \* \*

UNITED STATES PATENT AND TRADEMARK OFFICE
CERTIFICATE OF CORRECTION

PATENT NO.        : 8,394,766 B2
APPLICATION NO.   : 12/968120
DATED             : March 12, 2013
INVENTOR(S)       : Michael McCarthy and Marc Rose It is certified that error appears in the above-identified patent and that said Letters Patent is hereby corrected as shown below:

In the Claims
In Col. 8, line 65
replace "...of 10%+3% such..."
with "...of 10%±3% such...".

Signed and Sealed this
Eighteenth Day of June, 2013

Teresa Stanek Rea
*Acting Director of the United States Patent and Trademark Office*